(12) United States Patent
Mangion et al.

(10) Patent No.: US 8,153,678 B2
(45) Date of Patent: Apr. 10, 2012

(54) PROCESS FOR PREPARING A 3-PYRROLE SUBSTITUTED 2-INDOLINONE MALATE SALT

(75) Inventors: Bernardino Mangion, Santa Lucia (MT); Stephen Benedict David Winter, Barcelona (ES)

(73) Assignee: Medichem, S.A. (ES)

( * ) Notice: Subject to any disclaimer, the term of this patent is extended or adjusted under 35 U.S.C. 154(b) by 0 days.

(21) Appl. No.: 12/483,856

(22) Filed: Jun. 12, 2009

(65) Prior Publication Data

US 2009/0318525 A1  Dec. 24, 2009

Related U.S. Application Data

(60) Provisional application No. 61/061,430, filed on Jun. 13, 2008.

(51) Int. Cl.
*A61K 31/404* (2006.01)
*C07D 403/06* (2006.01)
*C07D 207/327* (2006.01)

(52) U.S. Cl. .......................... 514/414; 548/468; 548/537

(58) Field of Classification Search .................. 548/452, 548/468, 537; 514/412, 414
See application file for complete search history.

(56) References Cited

U.S. PATENT DOCUMENTS

| 6,573,293 B2 * | 6/2003 | Miller et al. .................. 514/414 |
| 7,435,832 B2 | 10/2008 | Hawley et al. |
| 2007/0191458 A1 | 8/2007 | Hawley et al. |

FOREIGN PATENT DOCUMENTS

WO  WO 2009/109388 A1  9/2009

OTHER PUBLICATIONS

*SKB* v. *Apotex*, U.S. Court of Appeals for the Federal Circuit, Feb. 24, 2006.*

* cited by examiner

*Primary Examiner* — Joseph Kosack
(74) *Attorney, Agent, or Firm* — Leydig, Voit & Mayer, Ltd.

(57) ABSTRACT

The invention relates to the malic acid salt of N-[2-(diethylamino)ethyl]-5-formyl-2,4-dimethyl-1H-pyrrole-3-carboxamide, to the use thereof as an intermediate for preparing the malic acid salt of sunitinib, and to pharmaceutical compositions comprising said malic acid salt of sunitinib.

13 Claims, 2 Drawing Sheets

PROCESS FOR PREPARING A 3-PYRROLE SUBSTITUTED 2-INDOLINONE MALATE SALT

CROSS-REFERENCE TO A RELATED APPLICATION

This patent application claims the benefit of U.S. Provisional Patent Application No. 61/061,430, filed Jun. 13, 2008, which is incorporated by reference.

BACKGROUND OF THE INVENTION

Sunitinib (compound I) is the international commonly accepted name for N-[2-(diethylamino)ethyl]-5-[(Z)-(5-fluoro-1,2-dihydro-2-oxo-3H-indol-3-yliden)methyl]-2,4-dimethyl-1H-pyrrole-3-carboxamie, and has an empirical formula of $C_{22}H_{27}FN_4O_2$, and a molecular weight of 398.47 g/mol. Sunitinib is an active pharmaceutical substance indicated for the treatment of abnormal cell growth, such as cancer, in mammals, particularly in humans.

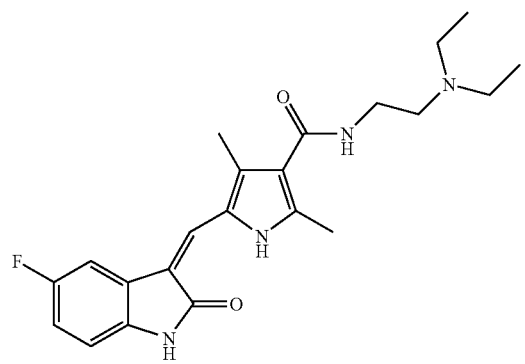

(I)

The malic acid salt of sunitinib has been selected for medical purpose and is commercially marketed under the trade name of SUTENT™ for the treatment of renal cell carcinoma and gastrointestinal stromal tumor.

Sunitinib base and its malate salt are described in U.S. Pat. No. 6,573,293 ("the '293 patent"), which is incorporated herein by reference. In particular, Example 80 of the '293 patent describes the preparation of sunitinib base via condensation of 5-formyl-2,4-dimethyl-1H-pyrrole-3-carboxylic acid(2-diethylaminoethyl)amide (compound II) and 5-fluoro-1,3-dihydroindol-2-one (compound III), which may be depicted as in Scheme 1. However, the '293 patent provides no additional details regarding the reaction conditions except a general synthetic procedure elsewhere in the patent.

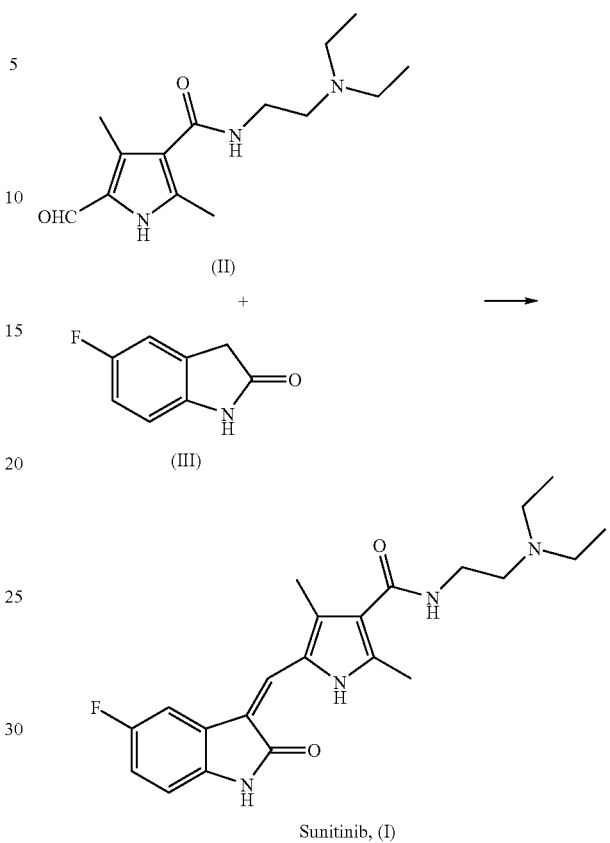

Scheme 1

Example 1 of U.S. Patent Application Publication No. 2007/0191458A1 ("the '458 publication") describes the preparation of sunitinib malate by reacting sunitinib base with malic acid in the presence of methanol as a solvent (the crystalline form of sunitinib malate obtained has been denominated therein as Form I). The '458 publication is incorporated herein by reference.

Applicants have observed that sunitinib base has a low solubility profile, which makes its dissolution and treatment for the preparation of the corresponding pharmaceutically acceptable salts (e.g., sunitinib malate) cumbersome. In this regard, the low solubility of sunitinib base requires large amounts of solvents or mixture of solvents and/or the use of particular harsh conditions aimed to increase the solubility of sunitinib base and/or reduce long reaction times, which represents a significant drawback, especially for industrial scale-up. Further, solid sunitinib base is difficult to handle since it is a very fine powder which is difficult to filter and isolate.

Thus, there is an unmet need for a process for preparing the malic acid salt of sunitinib which does not require the processing of sunitinib base, and which might be suitable for industrial implementation.

BRIEF SUMMARY OF THE INVENTION

The invention provides a malic acid salt of N-[2-(diethylamino)ethyl]-5-formyl-2,4-dimethyl-1H-pyrrole-3-carboxamide, compound of formula II, to the use thereof as an intermediate for preparing the malic acid salt of sunitinib, and to pharmaceutical compositions comprising the malic acid salt of sunitinib.

Applicants have surprisingly discovered that the malic acid salt of compound II, which is a new compound that has not been previously described, can be used for preparing the malic acid salt of sunitinib. Surprisingly, applicants have observed that the malate counterion of compound II is preserved during the conversion of compound II into sunitinib without giving rise to side-reactions. Therefore, the process of the invention is rapid, concise, and avoids the obtaining, isolation, and processing of sunitinib base, and hence overcomes one or more of the drawbacks associated with the lower solubility profile and difficult handling of solid sunitinib base. Further, the process of the invention provides a malic acid salt of sunitinib with high purity and high yield. Consequently, the process of the invention is cost-effective and suitable for industrial implementation.

DETAILED DESCRIPTION OF THE INVENTION

Figure 1:
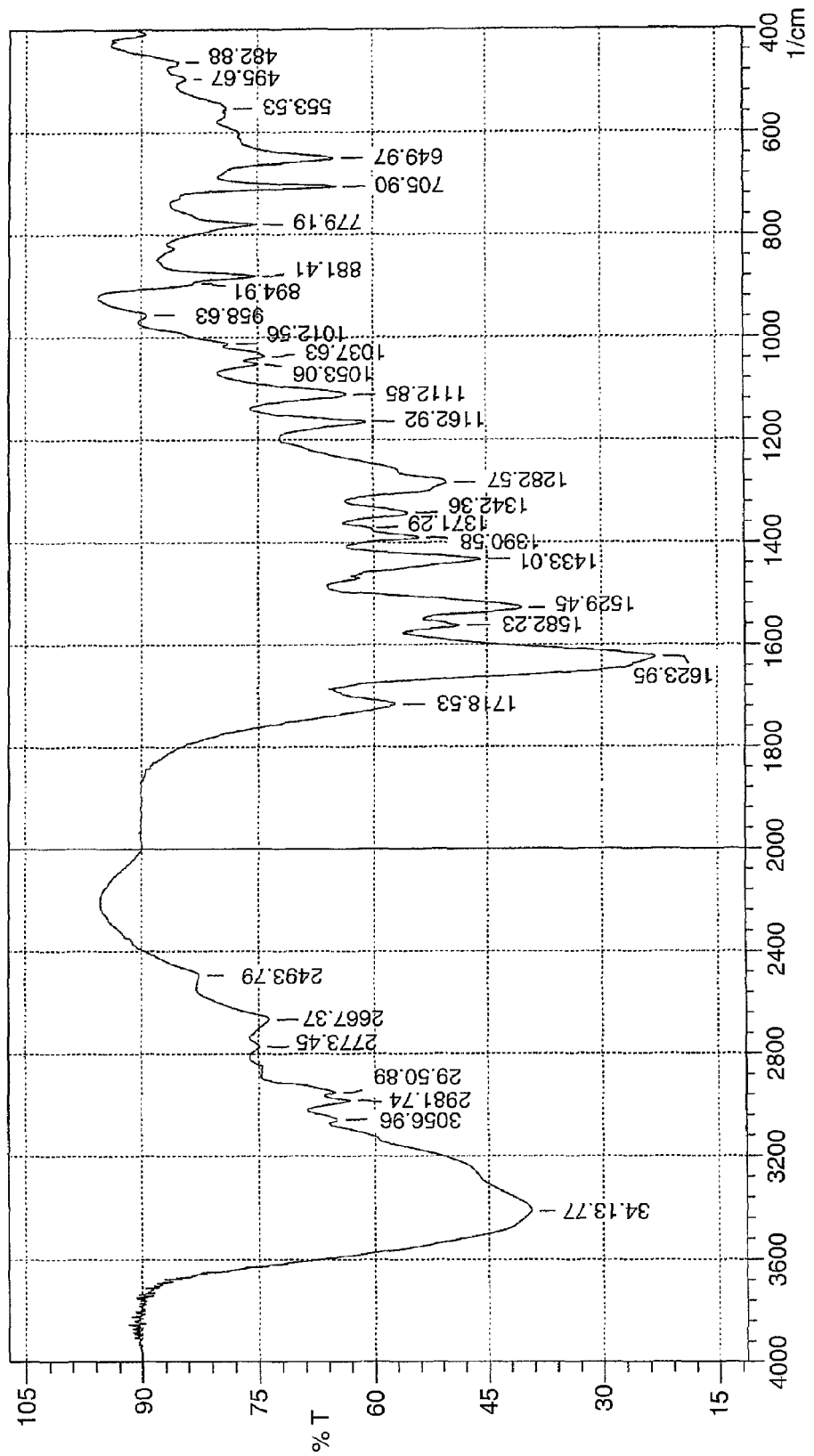
FIG. 1 is an infrared spectrum of the malic acid salt of 5-formyl-2,4-dimethyl-1H-pyrrole-3-carboxylic acid (2-diethylaminoethyl) amide, the compound of Formula (II), which is an intermediate in the preparation of the malic acid salt of sunitinib in accordance with an embodiment of the invention.

In an embodiment, the present invention provides a process for preparing the malic acid salt of sunitinib (malic acid salt of compound of Formula I),

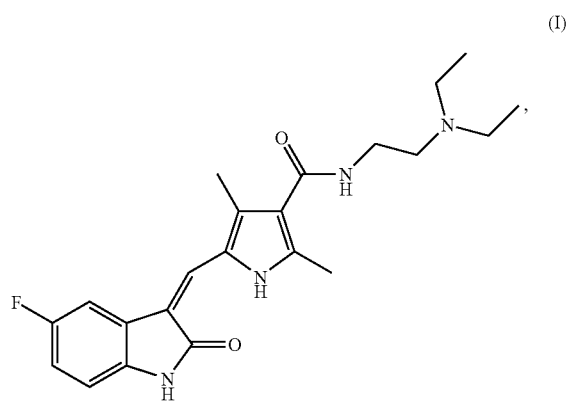

the process comprising treating the malic acid salt of 5-formyl-2,4-dimethyl-1H-pyrrole-3-carboxylic acid(2-diethylaminoethyl)amide (malic acid salt of compound of formula II),

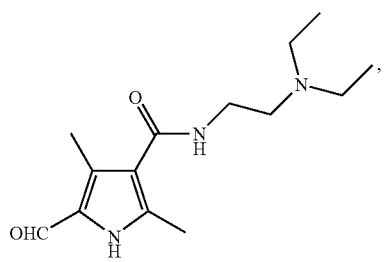

with 5-fluoro-1,3-dihydroindol-2-one (compound of formula III),

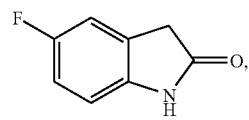

in the presence of an organic solvent and an organic amine.

The organic solvent of the process of the invention preferably comprises a $C_1$-$C_5$ alcohol solvent, and more preferably comprises n-butanol.

The organic amine of the process of the invention is preferably a secondary organic amine, and more preferably is pyrrolidine.

The organic amine of the process of the invention is preferably present in an amount suitable for carrying out the reaction. More preferably, the organic amine of the process of the invention is present in catalytic amounts.

The malic acid salt of compound I obtained according to a process of the invention has a purity higher than 99.5% as measured by HPLC.

In another embodiment, the invention provides the malic acid salt of 5-formyl-2,4-dimethyl-1H-pyrrole-3-carboxylic acid (2-diethylaminoethyl) amide (malic acid salt of compound of formula II).

In another embodiment, the present invention provides a process for preparing the malic acid salt of compound II of the invention, said process comprising
(i) combining compound of formula II with malic acid in the presence of a solvent, and
(ii) optionally, removing the solvent from the mixture.

The solvent of the process above preferably comprises a $C_1$-$C_5$ alcohol solvent, and more preferably comprises n-butanol.

In yet another embodiment, the present invention provides a process for preparing the malic acid salt of sunitinib (malic acid salt of compound of formula I), said process comprising reacting the malic acid salt of compound II of the invention with compound III.

The malic acid salt of compound II for use in the process of the invention above can be prepared in situ.

In yet another embodiment, the present invention provides a one-pot process for preparing the malic acid salt of sunitinib via the malic acid salt of compound II, said process comprising (i) combining compound of formula II with malic acid in the presence of an organic solvent, to obtain a mixture comprising the malic acid salt of compound II, and (ii) reacting the said mixture comprising the malic acid salt of compound II with compound III in the presence of an organic amine.

Surprisingly, the presence of a slight excess of free malic acid in the mixture comprising the malic acid salt of compound II of step (i) of the one-pot process above does not adversely affect the reaction of step (ii), giving rise to the malic acid salt of sunitinib with high yield.

The organic solvent of step (i) of the process above preferably comprises a $C_1$-$C_5$ alcohol solvent, and more preferably comprises n-butanol.

The organic amine of step (ii) of the process above is preferably a secondary organic amine, and more preferably is pyrrolidine.

The organic amine of step (ii) of the process above is preferably present in an amount suitable for carrying out the reaction. More preferably, the organic amine of step (ii) of the process above is present in catalytic amounts.

In still yet another embodiment, the present invention provides a pharmaceutical composition comprising the malic acid salt of sunitinib obtained according to the process of the invention.

EXAMPLES

General Experimental Conditions

Potentiometric Assay for the malic acid salt of compound II. A sample (about 400 mg) was weighed and dissolved in glacial acetic acid (80 mL). The solution was titrated with 0.1 N $HClO_4$ VS to determine the end-point potentiometrically. A blank determination was performed, and corrections, if any, were made. Using these conditions, each mL of 0.1 N $HClO_4$ VS is equivalent to 39.944 mg of the malic acid salt of 5-formyl-2,4-dimethyl-1H-pyrrole-3-carboxylic acid (2-diethylaminoethyl) amide. Calculations were made with reference to the dry substance.

Potentiometric Assay for the malic acid salt of sunitinib. A sample (about 500 mg) was weighed accurately and dissolved in glacial acetic acid (80 mL). The solution was titrated with 0.1 N $HClO_4$ VS to determine the end-point potentiometrically. A blank determination was performed and corrections, if any, were made. Using these conditions, each mL 0.1 N $HClO_4$ VS is equivalent to 53.256 mg of sunitinib malate. Calculations were made with reference to the dry substance.

Fourier Transform Infrared (FT-IR). FTIR spectra were acquired on a Shimadzu FT-IR 8400S spectrophotometer as potassium bromide (KBr) discs.

HPLC Method. HPLC analyses were conducted on a Shimadzu Prominence LC-20 system using the following conditions: column: XTerra MS C18, 5 µm, 4.6×150 mm; flow rate: 1 mL/min; detector: UV 265 nm; mobile phase A: 99.8:0.2 10 mM ammonium bicarbonate, pH 7.5: triethylamine; mobile phase B: acetonitrile; gradient: 85% A (0 min)-85% A (6 min)-70% A (21 min)-70% A (50 min)-85% A (55 min)-85% A (65 min); temperature: ambient; sample: 1.5 mg/mL in 25:75 mobile phase A:mobile phase B; and injection volume: 10 µL.

Example 1

Preparation of the malic acid salt of 5-formyl-2,4-dimethyl-1H-pyrrole-3-carboxylic acid(2-diethylaminoethyl)amide (Malic Acid Salt of Compound of Formula II)

This example describes the preparation and isolation of the malic acid salt of compound II in accordance with an embodiment of the invention.

7.05 g of 5-formyl-2,4-dimethyl-1H-pyrrole-3-carboxylic acid (2-diethylaminoethyl) amide and 21 mL of n-butanol were heated to dissolution. At 57° C. a brown, slightly opaque solution was obtained and a previously prepared solution of 3.89 g L-(−)-malic acid and 20 mL of n-butanol was added dropwise, maintaining the temperature of the reaction mixture. The resulting solution was stirred for 30 minutes and then cooled to room temperature. A gummy solid was formed at 25° C. Heating the mixture to dissolution (33° C.) and cooling again produced the same gummy solid. Finally, heating the mixture to 35° C. a brownish solid started to crystallize to give a very thick suspension. An additional 35 mL of n-butanol were then added, the reaction mixture was heated to 42° C. and cooled to 0-5° C. After stirring for 1 h at 0-5° C., the suspension was filtered, the collected solid was washed with 2×14 mL of n-butanol and then dried at 60° C. for 4 h under vacuum, to give 10.00 g (94.9% yield) of a brownish solid, which was the malic acid salt of compound of formula II.

Analytical data: IR (KBr): characteristic peaks at ($cm^{-1}$): 3414, 3057, 2982, 2951, 2773, 2667, 2494, 1717, 1624, 1562, 1529, 1433, 1390, 1371, 1342, 1283, 1165, 1113, 1053, 1037, 1013, 957, 881, 779, 706, 650. See FIG. 1; potentiometric assay: 99.77%; HPLC: 99.82% (% area); melting point: 110.6-111.8° C.

Example 2

Preparation of the Malic Acid Salt of Sunitinib (Malic Acid Salt of Compound of Formula (I))

This example describes the preparation of the malic acid salt of sunitinib via reaction of the malic acid salt of compound II with compound III in accordance with an embodiment of the invention.

4.52 g of the malic acid salt of 5-formyl-2,4-dimethyl-1H-pyrrole-3-carboxylic acid (2-diethylaminoethyl) amide obtained in Example 1, 1.70 g of 5-fluoro-1,3-dihydroindol-2-one and 60 mL of n-butanol were stirred at room temperature. 46.5 µL of pyrrolidine were then added and the suspension was heated to reflux. Complete dissolution of the materials was observed at 79° C. Once at reflux, an orange solid started to crystallize. The reaction was monitored by TLC and after 2.25 h at reflux it was complete. The suspension was then cooled to 0-5° C., stirred for 1 h and filtered. The collected solid was washed with 2×9 mL of n-butanol and then dried at 60° C. for 4 h under vacuum to give 5.26 g (87.7% yield) of a light orange solid.

4.12 g of the dry solid obtained above and 20.6 mL of distilled water were heated to dissolution. At 78° C. a clear red solution was obtained. The solution was filtered to remove insolubles, and the filter was washed with 3 mL of water. The filtrate was heated to 75° C. and 30.9 mL 2-propanol were added dropwise, while maintaining the temperature of the mixture. Once the addition was complete, the mixture was cooled to room temperature and stirred for 1 h. Crystallization was observed at 35° C. The light orange suspension was then cooled to 0-5° C., stirred for 1 h and filtered. The collected solid was washed with 2×8.5 mL of 2-propanol, and then dried at 60° C. for 4 h under vacuum to give 3.72 g (90.3% yield) of a light orange solid, which was the malic acid salt of sunitinib. Overall yield: 75.1%.

Figure 2:
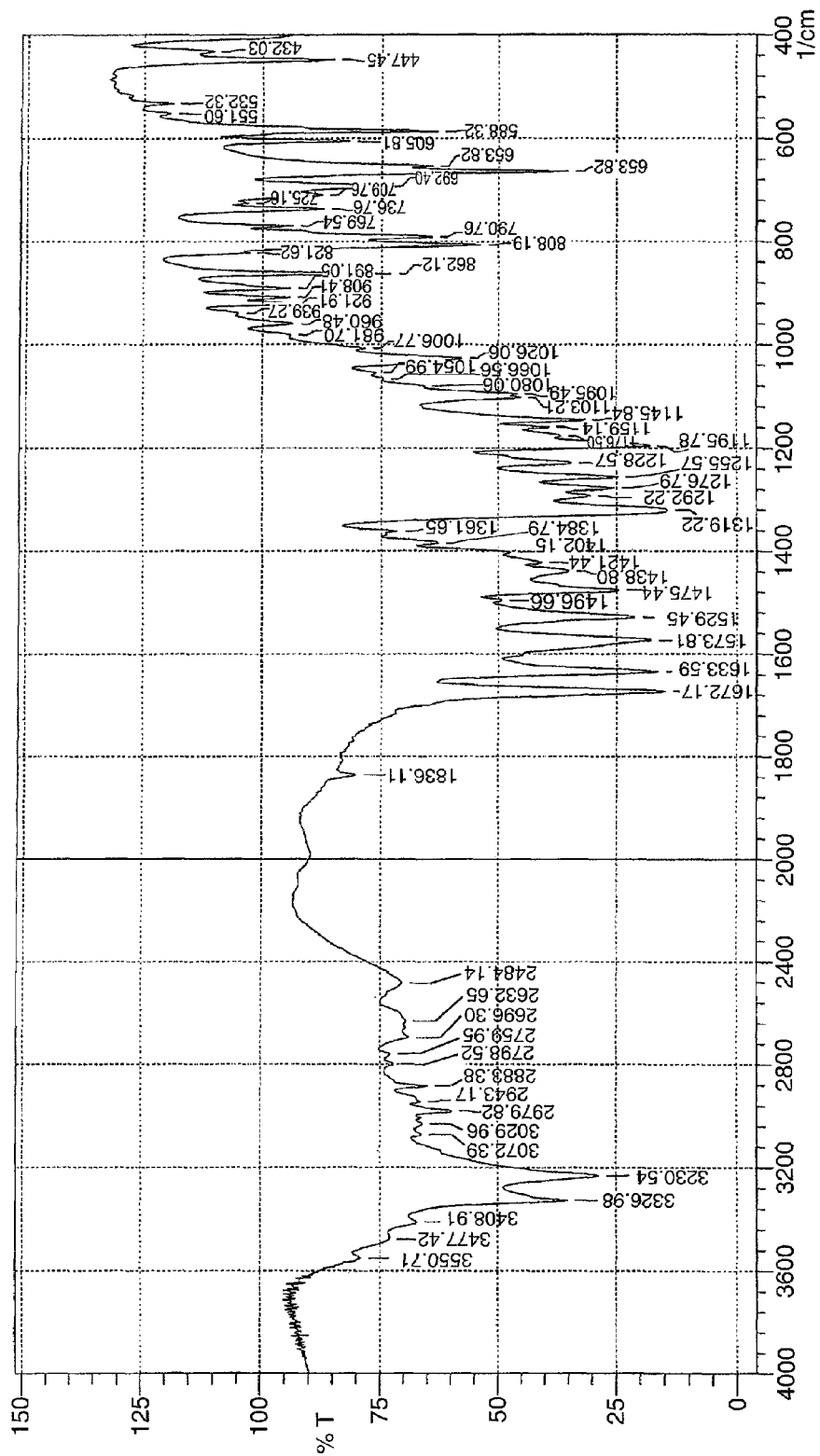
FIG. 2 is an infrared spectrum of the malic acid salt of sunitinib, in accordance with an embodiment of the invention.

Analytical data: IR (KBr): Characteristic peaks at (cm$^{-1}$): 3410, 3327, 3231, 2980, 2883, 2696, 2484, 1836, 1672, 1634, 1574, 1529, 1475, 1439, 1421, 1402, 1385, 1361, 1319, 1292, 1277, 1256, 1229, 1196, 1177, 1159, 1146, 1103, 1095, 1026, 960, 922, 908, 891, 862, 806, 791, 770, 737, 710, 692, 663, 654, 606, 586, 447. See FIG. 2; Potentiometric assay: 99.82%; HPLC: 99.78% (% area); Melting point: 188.9-189.9° C. Crystalline Form I.

Example 3

Preparation of the Malic Acid Salt of Sunitinib (Malic Acid Salt of Compound of Formula (I))

In accordance with an embodiment of the invention, this example describes the preparation of the malic acid salt of sunitinib via (i) preparation of the malic acid salt of compound II without isolation, and (ii) reaction of the non-isolated malic acid salt of compound II with compound III.

2.50 g of 5-formyl-2,4-dimethyl-1H-pyrrole-3-carboxylic acid (2-diethylaminoethyl) amide and 25 mL of n-butanol were heated to 48° C. to completely dissolve the solid. A previously prepared solution of 1.50 g L-(−)-malic acid and 7.5 mL of n-butanol was then added dropwise to the reaction mixture while maintaining the reaction temperature. Once addition was complete stirring was continued for 15 minutes. A previously prepared solution of 1.43 g of 5-fluoro-1,3-dihydroindol-2-one and 20 mL n-butanol was then added dropwise while maintaining the temperature of the reaction mixture. After the addition was complete 40 μL of pyrrolidine were added and the mixture was heated to 94° C. After 20 minutes at 94° C. an orange solid started to crystallize. The reaction was monitored by TLC and after 2.5 h at 94° C. the mixture was cooled to 0-5° C. and stirred for 1 h. The orange suspension was then filtered, the collected solid was washed with 2×8 mL of n-butanol and then dried at 60° C. for 4 h under vacuum to give 3.92 g (78.1% yield) of a light orange solid.

3.16 g of the dry solid obtained previously and 15.8 mL of distilled water were heated to dissolution. At 77° C. a clear red solution was obtained. The solution was filtered to remove insolubles, and the filter was washed with 4.25 mL of water. The filtrate was heated to 75° C. and 23.7 mL of 2-propanol were added dropwise, while maintaining the temperature of the mixture. Once the addition was complete, the mixture was cooled to room temperature and stirred for 1 h. Crystallization was observed at 26° C. The light orange suspension was then cooled to 0-5° C., stirred for 1 h and filtered. The collected solid was washed with 2×6.4 mL of 2-propanol, and then dried at 60° C. for 4 h under vacuum to give 2.88 g (91.1% yield) of a light orange solid, which was the malic acid salt of sunitinib. Overall yield: 71.2%.

Analytical data: IR (KBr): Essentially identical to the IR spectrum shown in FIG. 2; Potentiometric assay: 100.07%; HPLC: 99.56% (% area); Melting point: 188.3-189.1° C. Crystalline Form I.

Example 4

Preparation of the Malic Acid Salt of Sunitinib (Malic Acid Salt of Compound of Formula I)

In accordance with an embodiment of the invention, this example describes the preparation of the malic acid salt of sunitinib via (i) preparation of the malic acid salt of compound II without isolation, and (ii) reaction of the non-isolated malic acid salt of compound II with compound III.

75.00 g (0.283 mol) of N-[2-(diethylamino)ethyl]-5-formyl-2,4-dimethyl-1H-pyrrole-3-carboxamide, 45.47 g (0.339 mol) of L-(−)-malic acid and 375 mL of n-butanol were heated to 70-80° C. until a solution was obtained.

Separately, 42.71 g (0.283 mol) of 5-fluoro-1,3-dihydro-2H-indol-2-one and 375 mL of n-butanol were heated to 70-80° C. and stirred until a solution was obtained. 1.16 mL (1.00 g, 0.014 mol) of pyrrolidine was added to the solution. The 5-fluoro-1,3-dihydro-2H-indol-2-one solution was then added to the solution of N-[2-(diethylamino)ethyl]-5-formyl-2,4-dimethyl-1H-pyrrole-3-carboxamide and L-(−)-malic acid.

Once the addition was complete, the clear solution obtained was heated to reflux. Once at reflux, an orange solid started to crystallize to give a thick orange suspension. After 4 h at reflux, the mixture was cooled to 10-15° C. and stirred for 1 h at this temperature. The light orange suspension was then filtered and the collected solid was washed with 2×112.5 mL of n-butanol to give 240.75 g of crude product (LOD=39.92%, 144.64 g dry, 96.1% yield) as a light orange solid.

A mixture of the crude product and distilled water (433.9 mL) was heated to 70° C., at which temperature a clear, red solution was obtained. The solution was cooled to 56° C. and filtered to remove insolubles. The filter was washed with 43.4 mL of water. The filtrate was heated to 50-55° C. and 289.3 mL of 2-propanol was added drop-wise, while maintaining the temperature of the mixture. Once the addition was complete, the mixture was cooled to 20-25° C. over a period of 1 h. The light orange suspension obtained was cooled to 10-15° C., stirred for 1 h and filtered. The collected solid was washed with 2-propanol (2×217.0 mL), and then dried at 60° C. for 4 h under vacuum to give 125.11 g (86.5% yield) of sunitinib malate as a light orange solid. Overall yield: 83.1%.

Analytical data: IR (KBr): Essentially identical to FIG. 2; Potentiometric assay: 99.86%; HPLC: 99.62% (% area); Melting point: 189.0-189.9° C.

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A process for preparing the malic acid salt of sunitinib (malic acid salt of compound of formula I),

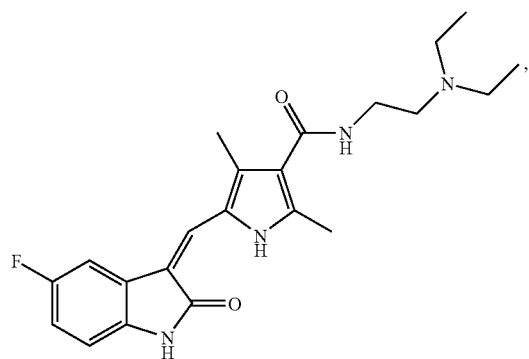

(I)

said process comprising treating the malic acid salt of 5-formyl-2,4-dimethyl-1H-pyrrole-3-carboxylic acid (2-diethylaminoethyl) amide (malic acid salt of compound of formula II),

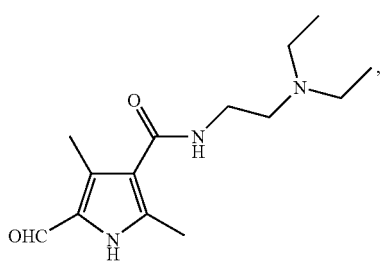

(II)

with 5-fluoro-1,3-dihydroindol-2-one (compound of formula III),

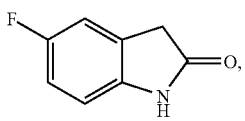

(III)

in the presence of an organic solvent and an organic amine.

2. The process of claim 1, wherein the organic solvent comprises a $C_1$-$C_5$ alcohol solvent.

3. The process of claim 1, wherein the organic solvent comprises n-butanol.

4. The process of claim 1, wherein the organic amine is a secondary organic amine.

5. The process of claim 4, wherein the secondary organic amine is pyrrolidine.

6. Malic acid salt of 5-formyl-2,4-dimethyl-1H-pyrrole-3-carboxylic acid (2-diethylaminoethyl) amide (malic acid salt of compound of formula (II)),

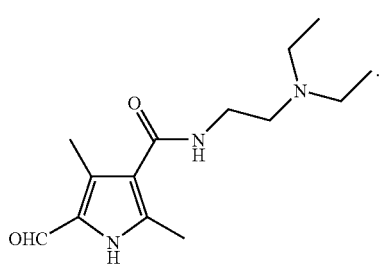

(II)

7. A process for preparing the malic acid salt of compound (II) of claim 6, said process comprising contacting a compound of formula (II) with malic acid.

8. The process of claim 7, wherein the contacting is carried out in an organic solvent.

9. The process of claim 7, wherein the organic solvent comprises a $C_1$-$C_5$ alcohol solvent.

10. The process of claim 9, wherein the $C_1$-$C_5$ alcohol solvent comprises n-butanol.

11. A process for preparing a malic acid salt of sunitinib, said process comprising reacting a malic acid salt of 5-formyl-2,4-dimethyl-1H-pyrrole-3-carboxylic acid (2-diethylaminoethyl) amide with a dihydroindol-2-one compound.

12. The process of claim 1, wherein the malic acid salt of the compound of formula II is prepared in situ.

13. The process of claim 11, wherein the malic acid salt of 5-formyl-2,4-dimethyl-1H-pyrrole-3-carboxylic acid (2-diethylaminoethyl) amide is prepared in situ.

* * * * *